United States Patent [19]
Flynn et al.

[11] Patent Number: 5,899,930
[45] Date of Patent: May 4, 1999

[54] TRIPLE PORT AND QUADRUPLE PORT IN-LINE HEADER DESIGNS

[75] Inventors: David M. Flynn, Lino Lakes; Andra Thomas, Minneapolis; Larry Hum, Cottage Grove, all of Minn.

[73] Assignee: Cardiac Pacemakers, Inc., St. Paul, Minn.

[21] Appl. No.: 08/939,750

[22] Filed: Sep. 29, 1997

[51] Int. Cl.⁶ .................................................. A61N 1/375
[52] U.S. Cl. ................................................................ 607/37
[58] Field of Search ................................. 607/37, 5, 9, 36

[56] References Cited

U.S. PATENT DOCUMENTS

| | | |
|---|---|---|
| 4,105,037 | 8/1978 | Richter et al. . |
| 4,310,001 | 1/1982 | Comben . |
| 4,934,366 | 6/1990 | Truex et al. . |
| 5,336,246 | 8/1994 | Dantanarayana ........................ 607/37 |
| 5,374,279 | 12/1994 | Duffin et al. ............................... 607/37 |
| 5,545,188 | 8/1996 | Bradshaw et al. ........................ 607/37 |
| 5,620,477 | 4/1997 | Pless et al. ................................ 607/37 |

Primary Examiner—Scott M. Getzow
Attorney, Agent, or Firm—Nikolai, Merserau & Dietz

[57] ABSTRACT

A triple port and quadruple port header assembly of an implantable tissue stimulator, such as a pacemaker, defibrillator, or nerve stimulator, wherein three or more sensing and/or pacing leads may be coupled thereto. Ports of the header assembly receive the terminal end of corresponding leads, wherein each port has two terminal blocks positioned therein which are adapted for coupling a pin and/or ring of the terminal end of the corresponding lead. Feedthrough wires electrically couple the terminal blocks to the electronic circuit of the implantable tissue stimulator, and jumper wires electrically couple the terminal blocks of at least two ports, thereby electrically coupling the corresponding pins and/or rings of at least two leads contained therein.

30 Claims, 9 Drawing Sheets

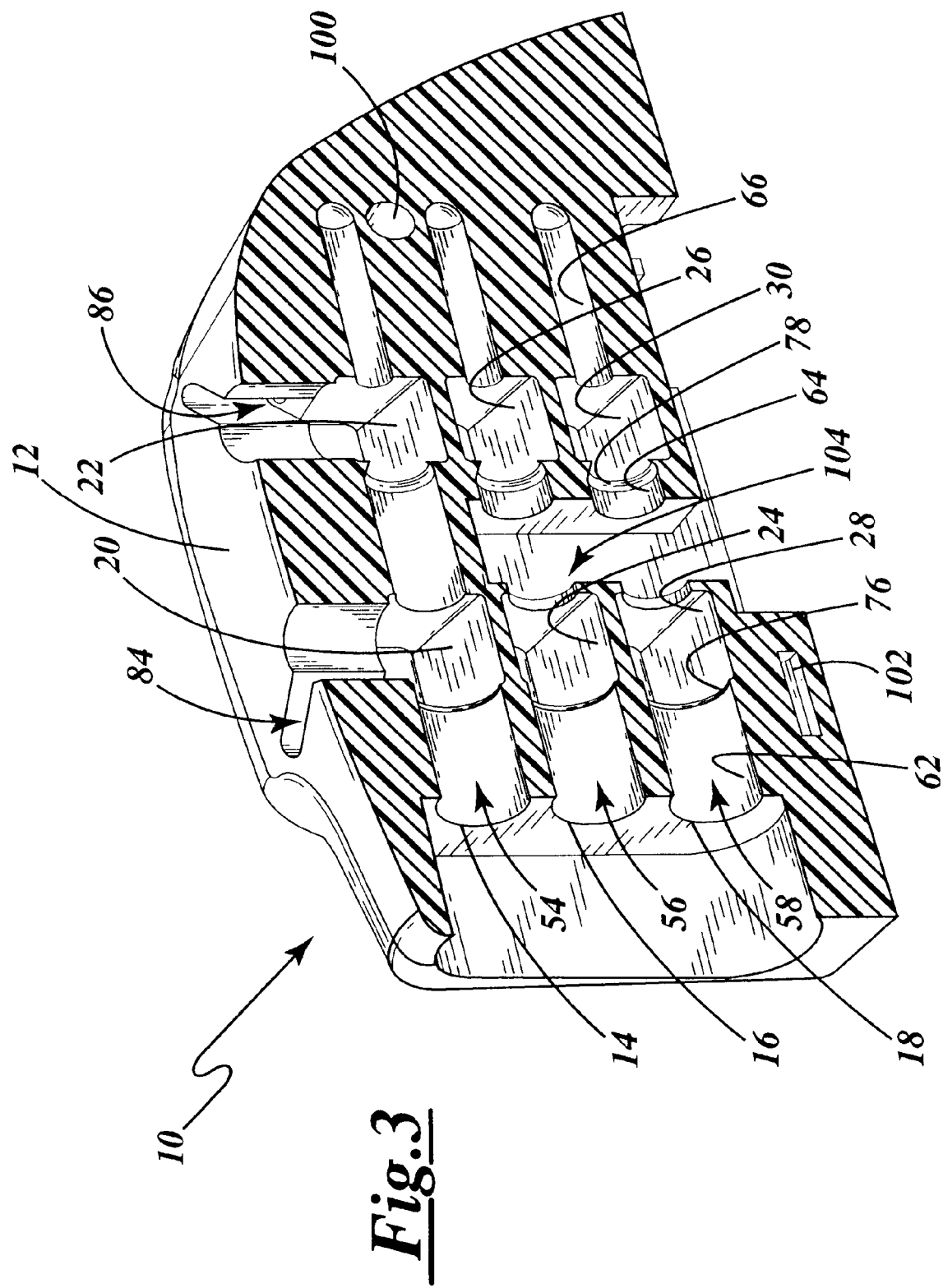

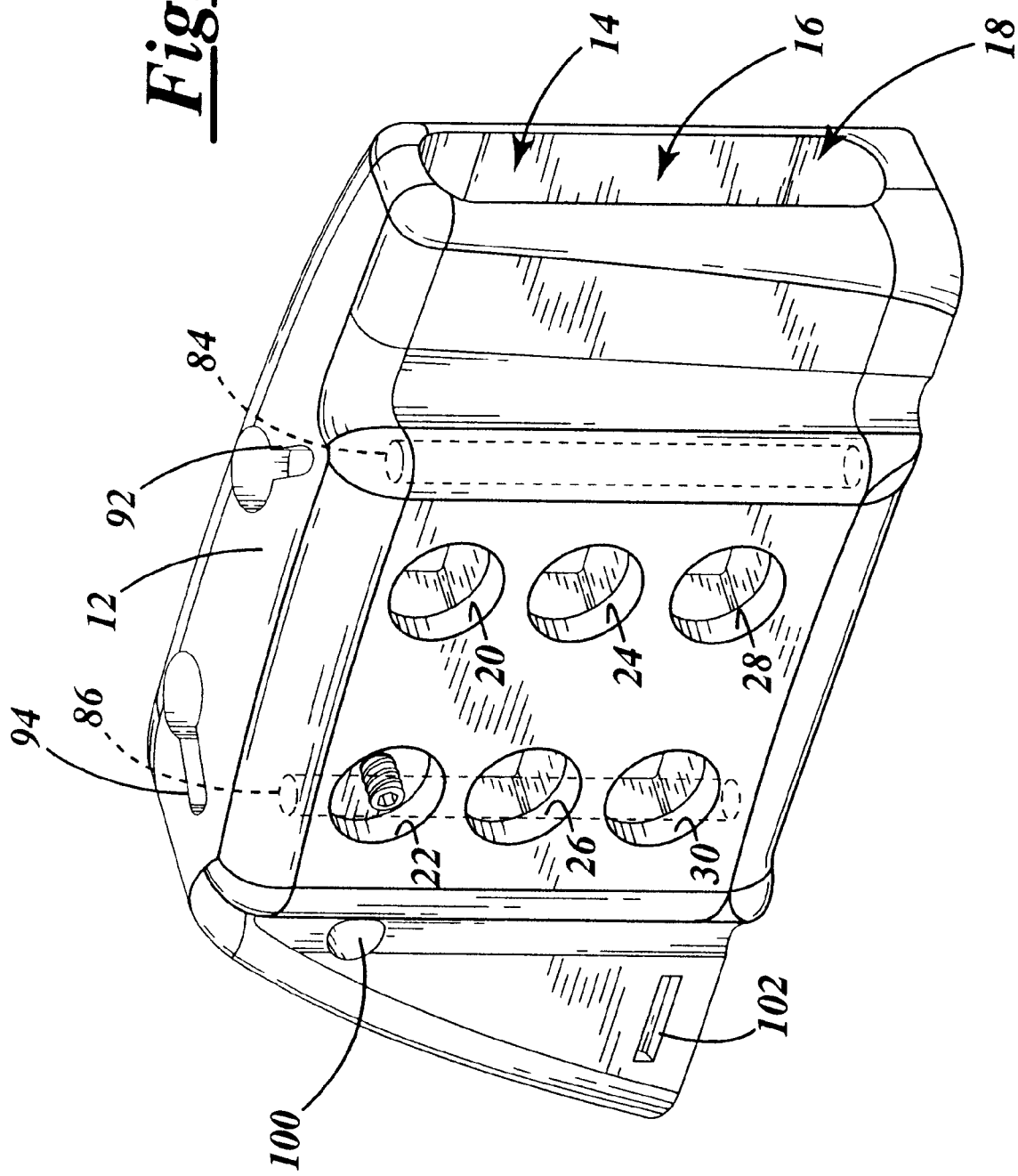

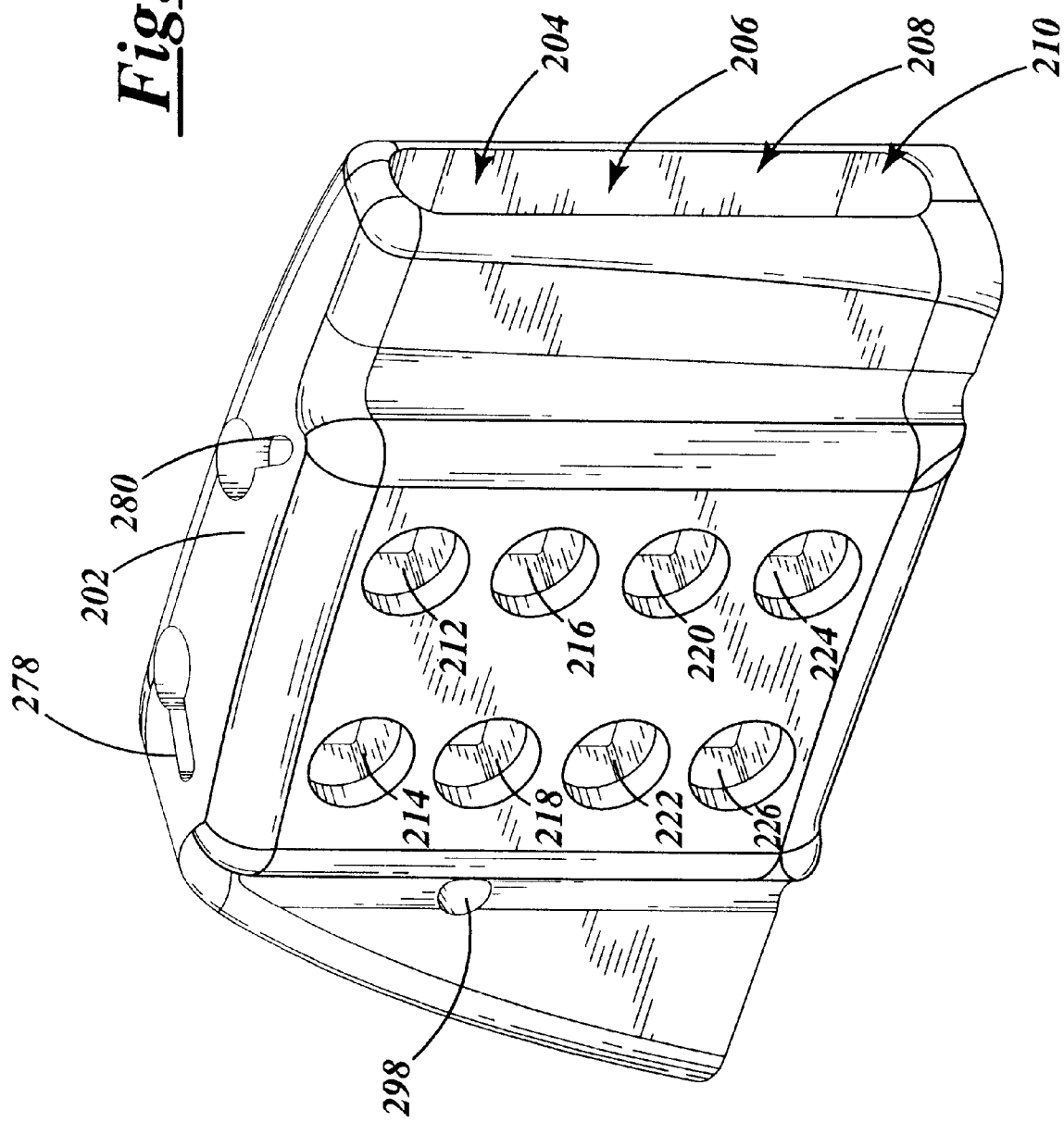

TRIPLE PORT AND QUADRUPLE PORT IN-LINE HEADER DESIGNS

BACKGROUND OF THE INVENTION

I. Field of the Invention

This invention relates generally to implantable cardiac rhythm management devices, and more particularly relates to a header assembly electrically and mechanically coupled to a pulse generator of the implantable device. The header assembly of the cardiac rhythm management device includes a housing having an electrically interconnected triple port or quadruple port formed in the housing, wherein each port is adapted for receiving a corresponding sensing and/or pacing lead. The electrically interconnected ports reduce the number of required hermetically sealing connections when the conductors of at least two sensing and/or pacing leads are electrically coupled together. Each port of the header assembly has two terminal blocks positioned therein, wherein each terminal block is adapted for coupling a pin and/or ring of the terminal end of each corresponding lead. Feedthrough wires electrically couple the terminal blocks to the electronic circuit of the pulse generator. Jumper wires electrically couple preselected terminal blocks of at least two ports, thereby electrically coupling the corresponding pins and/or rings of at least two leads, ultimately resulting in a simultaneous transmission of an identical signal to the electrically coupled leads.

II. Discussion of the Related Art

Various cardiac rhythm management devices capable of pacing or defibrillating a patient's heart comprise a pulse generator having an electronic circuit and power supply contained within a metal casing, commonly referred to as "the can". A lead, capable of transmitting a therapeutic electrical signal generated by the pulse generator to the heart, is electrically coupled to the electronic circuit of the pulse generator. A "header" having a receptacle or port is commonly provided in order to "plug" the lead into the rhythm management device and electrically couple the lead to the electronic circuit contained within the can. Over the years, the receptacles located in the header of the implantable cardiac rhythm management device and the terminal connector end of a corresponding lead have been standardized by the International Standards Organization (ISO). In the standard connector and receptacle arrangement, an elongated terminal socket or receptacle is formed in the header portion of the rhythm management device and an elongated connector adapted to be received in the receptacle is formed on the terminal end of the lead.

When two leads are required, a separate receptacle is formed in the header for each corresponding lead. Representative examples of such devices having two receptacles appear in U.S. Pat. No. 5,545,188, issued to Bradshaw et al. (hereinafter the '188 device) and U.S. Pat. No. 5,336,246, issued to Dantanarayana (hereinafter the '246 device). The '188 and '246 devices include a metal casing having a header assembly attached thereto. The header comprises two independent receptacles embedded in an insulating epoxy. The header is sealably attached to the can and each receptacle includes insulated contacts and conductive wire coupling the contacts to the electronic circuit contained within the can. Leads of suitable complimentary construction insert into respective receptacles. The first receptacle may be, for example, associated with atrial sensing and pacing and the second receptacle may be, for example, associated with ventricular sensing and pacing.

Currently, such cardiac rhythm management devices may be used, for example, to administer pacing therapy to a Congestive Heart Failure (CHF) patient having a higher degree of AV-block or an AV conduction disorder. The rhythm management device, suited for pacing the ventricle, may be used to administer the desired pacing therapy to the ventricle, synchronous with the intrinsic atrial rate. Such pacing therapy may require a lead associated with the right atrium, a lead associated with the left ventricle, and a lead associated with the right ventricle. In this instance, it is desirable to transmit the same pacing signal through both the left and right ventricular leads. In order to electrically couple the three leads to the two receptacles of the cardiac rhythm management device, it is current practice to interconnect the right and left ventricular leads with an adapter and sleeve. The adapter then plugs into a corresponding receptacle of the cardiac rhythm management device, wherein the pacing through the leads may be unipolar or extended bipolar pacing. Utilizing an adapter and sleeve to interconnect two or more leads increases the required number of sealing connections.

During implantation of a cardiac rhythm management device incorporating such an adapter for the leads, the physician must create a first pocket for the cardiac rhythm management device and a second pocket to hold the adapter and coiled leads. The second pocket is typically created in a separate plane from the pulse generator in order to decrease risk of erosion. The use of an adapter complicates the surgical procedure, increases the length of time in surgery and overall cost of implanting the device, and increases the chance of skin erosion and associated infection.

Hence, there is a need for a header assembly that eliminates the need to use an adapter to interconnect two or more leads without unduly increasing the overall size of the header housing. The present invention addresses these needs.

SUMMARY OF THE INVENTION

The purpose of the present invention is to provide a triple or quadruple port header capable of electrically coupling at least two electrical sensing and/or pacing leads. Without any limitation intended, the triple port or quadruple port headers of the present invention may be used with conventional CHF rhythm management devices. The header assembly of the present invention includes a housing, electrically conductive terminal blocks, at least one jumper wire, and feedthrough wires.

The housing has at least two ports each extending through the housing from a side surface of the housing towards but short of an opposite side surface. Each port is configured and adapted for sealably receiving a terminal end of a lead. The lead may be of a common design having a plurality of highly flexible conductors, extending through an insulating lead body, wherein a terminal pin and/or ring of suitable known construction is attached to the terminal end of the lead body.

Intersecting each port are spaced apart apertures into which electrically conductive terminal blocks are positioned. Bores extend through the terminal blocks and are sized to engage the terminal end of the lead. The terminal blocks include set screws to secure the terminal end of the lead within the terminal block and further create a conducting engagement between the terminal block and terminal end of the lead.

Feedthrough wires electrically couple the terminal blocks to the electronic circuit. A channel interconnects the apertures of at least two separate ports, wherein a conductive jumper wire is attached to the terminal blocks contained within the interconnected apertures. In this manner, at least two leads are electrically coupled such that a signal transmitted to one lead is also simultaneously transmitted to the interconnected lead. The housing assembly including feedthrough wires and jumper wires contained within the housing eliminates the need for an adapter to electrically couple two or more leads.

The housing is attached to a hollow titanium casing of the pulse generator. An electronic circuit and power supply are contained within the casing and together generate pacing or defibrillating signals. The contacts or terminal blocks of the header are electrically coupled to the electronic circuit contained within the casing to thereby transmit rhythm management signals through the electrically coupled leads.

Positioned between the header and electronic circuit is a feedthrough assembly which includes an insulative body and at least two conductive wires extending through the insulative body. A first end of each conductive wire is coupled to the electronic circuit and an opposite end is electrically coupled to an electrical contact or terminal block positioned within a port of the housing.

OBJECTS

It is accordingly a principal object of the present invention to provide a header assembly of an implantable device capable of electrically coupling at least two sensing and/or pacing leads without requiring an adapter.

Another object of the present invention is to provide a triple port or quadruple port header assembly of an implantable device, wherein at least two ports are interconnected to allow electrical coupling of associated leads.

Yet another object of the present invention is to provide a header assembly that eliminates the need to create a second pocket to hold an adapter and coiled leads, thereby decreasing the chance of skin erosion and associated infection, and increasing patient comfort.

Still another object of the present invention is to reduce the number of required hermetically sealing connections when the conductors of at least two sensing and/or pacing leads are electrically coupled together.

These and other objects and advantages of the present invention will become readily apparent to those skilled in the art from a review of the following detailed description of the preferred embodiment especially when considered in conjunction with the accompanying drawings in which like numerals in the several views refer to corresponding parts.

BRIEF DESCRIPTION OF THE DRAWINGS

FIG. 3 is a partial sectional view of the triple port header housing of the type shown in FIG. 1;

FIG. 4 is a back perspective view of the triple port header housing of the present invention having some of the terminal blocks removed for clarity;

FIG. 11 is a back perspective view of a quadruple port header housing of the present invention having the terminal blocks removed for clarity.

DETAILED DESCRIPTION

Referring first to FIGS. 1–4, a header assembly 10 of an implantable rhythm management device is shown. The header assembly 10 generally includes a non-conductive housing 12, ports 14–18, apertures 20–30 intersecting respective ports 14–18, electrically conductive terminal blocks 32–42 retained in corresponding apertures 20–30, feedthrough wires 44–50, and jumper wire 52.

Figure 5:
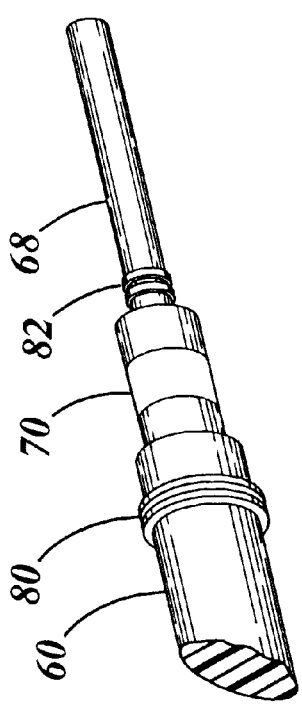
FIG. 5 is a perspective view of a bi-polar lead adaptable for use with the header housing of the present invention.
Figure 6:
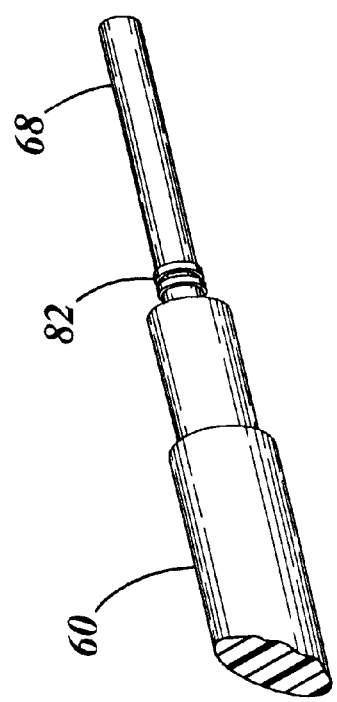
FIG. 6 is a perspective view of a uni-polar lead adaptable for use with the header housing of the present invention.

The housing 12 is preferably manufactured from a non-conductive medical grade polymer of known suitable composition, wherein the ports 14–18 and apertures 20–30 are formed into the housing 12. Each port 14–18 has a central bore, 54–58 respectively, adapted for receiving the terminal end of a lead 60. The corresponding bore 54–58 of each port 14–18 extends into the housing 12 from a side surface of the housing 12 toward but short of an opposite side surface. Each bore may be tapered or stepped having varying diameters to thereby fittingly receive the shape and size of the terminal end of the lead 60 (examples of suitable leads are further shown in FIGS. 5 and 6), wherein the largest diameter or step 62 may be approximately equal to the outer diameter of the lead 60 body, the middle diameter or step 64 being equal to the diameter of the lead's conductive ring 70, and the smallest diameter or step 66 may be dimensioned to receive the terminal pin 68 of the lead 60 (see FIGS. 1 and 3). The terminal end of the lead may manufactured in accordance with the International Organizations IS1 standards including the conductive pin 68 and ring 70 coupled to the lead.

Figure 7:
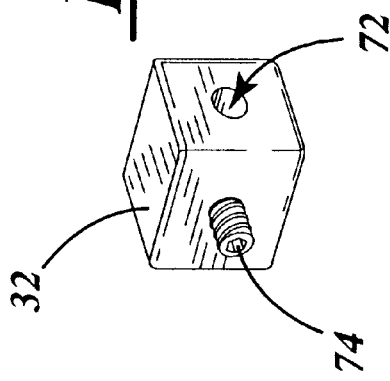
FIG. 7 is a back perspective view of a terminal block adaptable for use with the header housing of the present invention.

Apertures 20 and 22 intersect bore 54, apertures 24 and 26 intersect bore 56 and apertures 28 and 30 intersect bore 58 (see FIG. 3). Electrically conductive terminal blocks 32–42 are positioned within corresponding apertures 20–30 (see FIG. 2). Although terminal block 32 is shown in FIG. 7, those skilled in the art will appreciate that terminal blocks 34–42 may be of similar suitable construction. Each terminal block 32–42 has a bore 72 extending therethrough, wherein the bore 72 of each terminal block 32–42 aligns with the corresponding bore 54–58 of the respective port 14–18 and is sized to fittingly receive the associated portion of the terminal end of the lead. Adjacent the intersection between the bore 54–58 and respective apertures 20–30, tapering annular lips 76 and 78 extend perpendicularly inward from each bore 54–58. When a lead 60 is plugged into the port 14–18, shoulder seals 80 and 82 of the lead 60 engage the respective lips 76 and 78 thereby sealingly engaging the lead 60 to the housing 12 and electrically isolating various segments of the lead 60.

Each terminal block 32–42 contains a set screw 74 (see FIGS. 4 and 7). When the set screws 74 are tightened, the lead 60 is held in place in contact with the corresponding terminal block, thereby insuring mechanical and electrical contact between the lead 60 and terminal block. When a lead 60 is inserted into a desired port of the housing 12, the conductive ring 70 and terminal pin 68 of the lead are coupled electrically to the corresponding terminal block. Without any limitation intended, the terminal blocks 32–42, terminal pin 68, ring 70, feedthrough wires 44–50 and jumper wires 52 are manufactured from titanium or other conductive material sufficient to meet medical standards and all requirements of current transmission. The housing 12, insulative lead 60 body and shoulder seals 80–82 are manufactured from a known polymer or other elastomeric non-conductive material commonly used in the manufacture of implantable pacing/defibrillating devices and leads.

A conduit is formed in the housing for each feedthrough wire. Conduits 84 and 86 extend from the bottom of the housing through to the opposite top side of the housing (see FIGS. 2–4). Grooves 92 and 94 interconnect conduits 84 and 86 respectively. Feedthrough wires 44 and 46 extend from the bottom of the housing up through conduits 84 and 86 respectively, through grooves 92 and 94 and are attached to the corresponding terminal blocks 32 and 34. Conduits 84 and 86 are positioned towards the ends of the housing, to allow isolation of the terminal blocks 32–42 and feedthrough wires 44 and 46 extending through the housing 12 without unduly widening the housing. Conduits 88 and 90 extend from the bottom of the housing 12 and into apertures 28 and 30 respectively (see FIG. 1). Feedthrough wires 48 and 50 extend through conduits 88 and 90, interconnecting the electronic circuit of the pulse generator with the corresponding terminal blocks 40 and 42.

Figure 1:
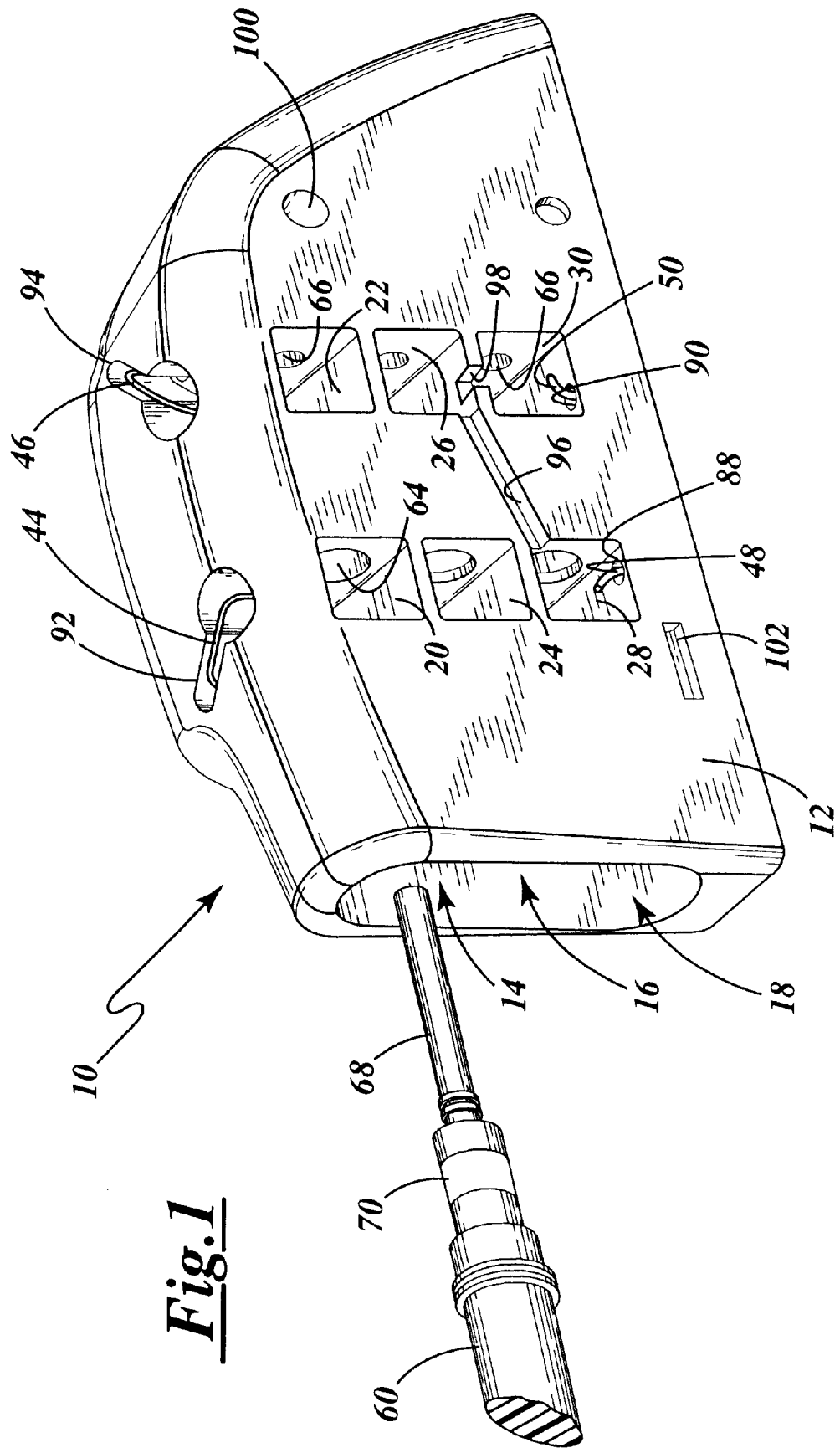
FIG. 1 is a front perspective view of a triple port header assembly of the present invention having the terminal blocks and jumper wire removed for clarity and further having a bipolar lead aligned with an upper port.
Figure 2:
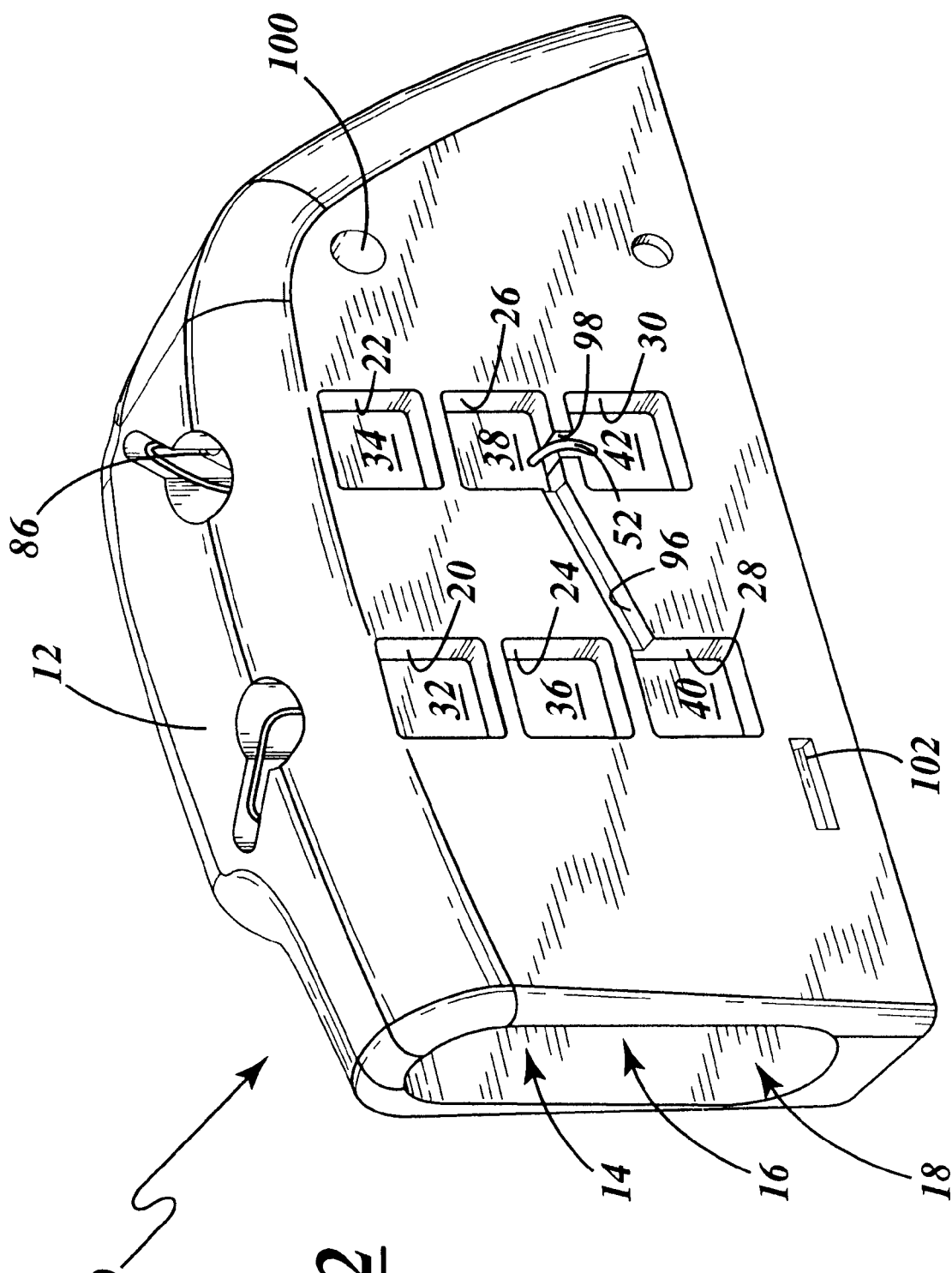
FIG. 2 is a front perspective view of the triple port header housing of the type shown in FIG. 1, with the terminal blocks positioned within the respective apertures.

A plurality of channels 96 and 98 are formed in the housing extending between and interconnecting aperture 26 to aperture 28 and aperture 26 to aperture 30 respectively (see FIGS. 1 and 2). A jumper wire 52 may be positioned within a channel 96 to thereby interconnect terminal block 38 to terminal block 40 or may be positioned within channel 98 to thereby interconnect terminal block 38 to terminal block 42. For example, the jumper wire 52 may be positioned in channel 96 and welded between terminal block 40 and terminal block 38, interconnecting the conductive ring 70 of a lead positioned in port 18 with the terminal pin 68 of a lead positioned in port 16. Likewise, a jumper wire 52 may positioned within channel 98 and welded between terminal blocks 38 and 42, interconnecting the terminal pin 68 of a lead positioned in port 16 with a terminal pin 68 of a lead positioned in port 18. Medical adhesive or epoxy may be applied to each of the exposed terminal block 32–42 surfaces and the channels 96 and 98 to thereby isolate the terminal blocks 32–42 and jumper wire 52 from fluid contact.

A passage 100 extends through the housing 12 and is adapted for receiving sutures therethrough, thereby providing a means for securing the housing 12 of the cardiac rhythm management device within a surgically formed pocket in the patient. Slots 102 are formed in a bottom portion of the housing 12 and are adapted for engaging with tabs (not shown) which extend from the casing of the cardiac rhythm management device, to thereby sealably secure the housing to the casing. Portions of the housing form voids, as at 104 (see FIG. 3), to thereby reduce both the weight of the housing 12 and the amount of materials required for the housing 12.

Figure 8:
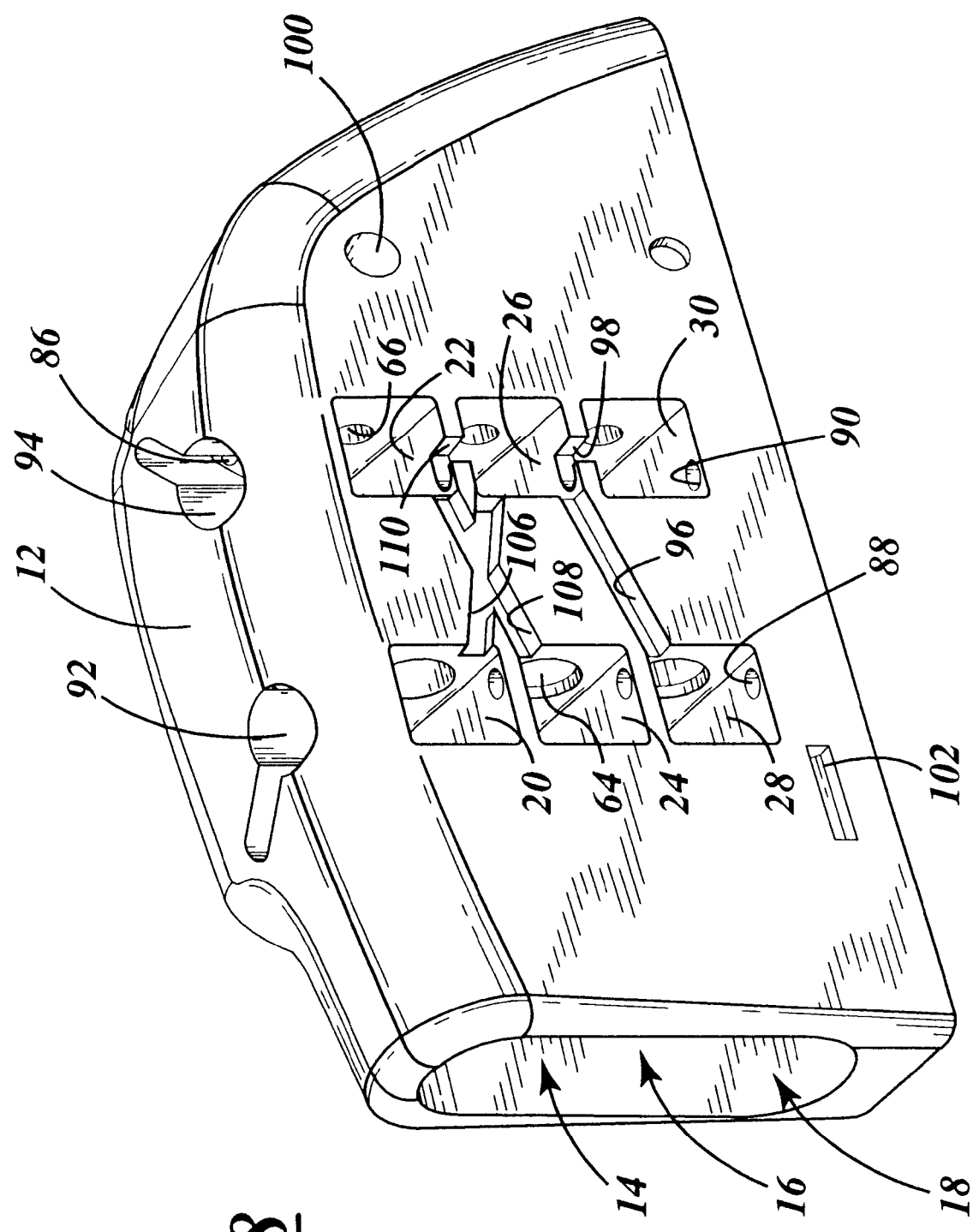
FIG. 8 is a front perspective view of an alternate embodiment of the triple port header housing of the present invention.

FIG. 8 shows an alternate embodiment of the housing having additional channels 106–110 formed in the housing. Channel 106 extends between apertures 20 and 26 to thereby interconnect terminal blocks 32 and 38, channel 108 extends between apertures 22 and 24 to thereby interconnect terminal blocks 34 and 36, and channel 110 extends between apertures 22 and 26 to thereby interconnect terminal blocks 34 and 38. A jumper wire may be positioned in channel 106 to electrically couple, for example, terminal block 32 and terminal block 38, allowing the conductive ring 70 of a lead positioned in port 14 to be electrically coupled to the terminal pin 68 of a lead positioned in port 16. Likewise, a jumper wire may be positioned in channel 108 to electrically couple terminal block 34 and terminal block 36, allowing the terminal pin 68 of a lead positioned in port 14 to be electrically coupled to a conductive ring 70 of a lead positioned in port 16. Alternatively, a jumper wire may be positioned in channel 110 to electrically couple terminal block 34 and terminal block 38, allowing the terminal pin 68 of a lead positioned in port 14 to be electrically coupled to the terminal pin 68 of a lead positioned in port 16.

Figure 9:
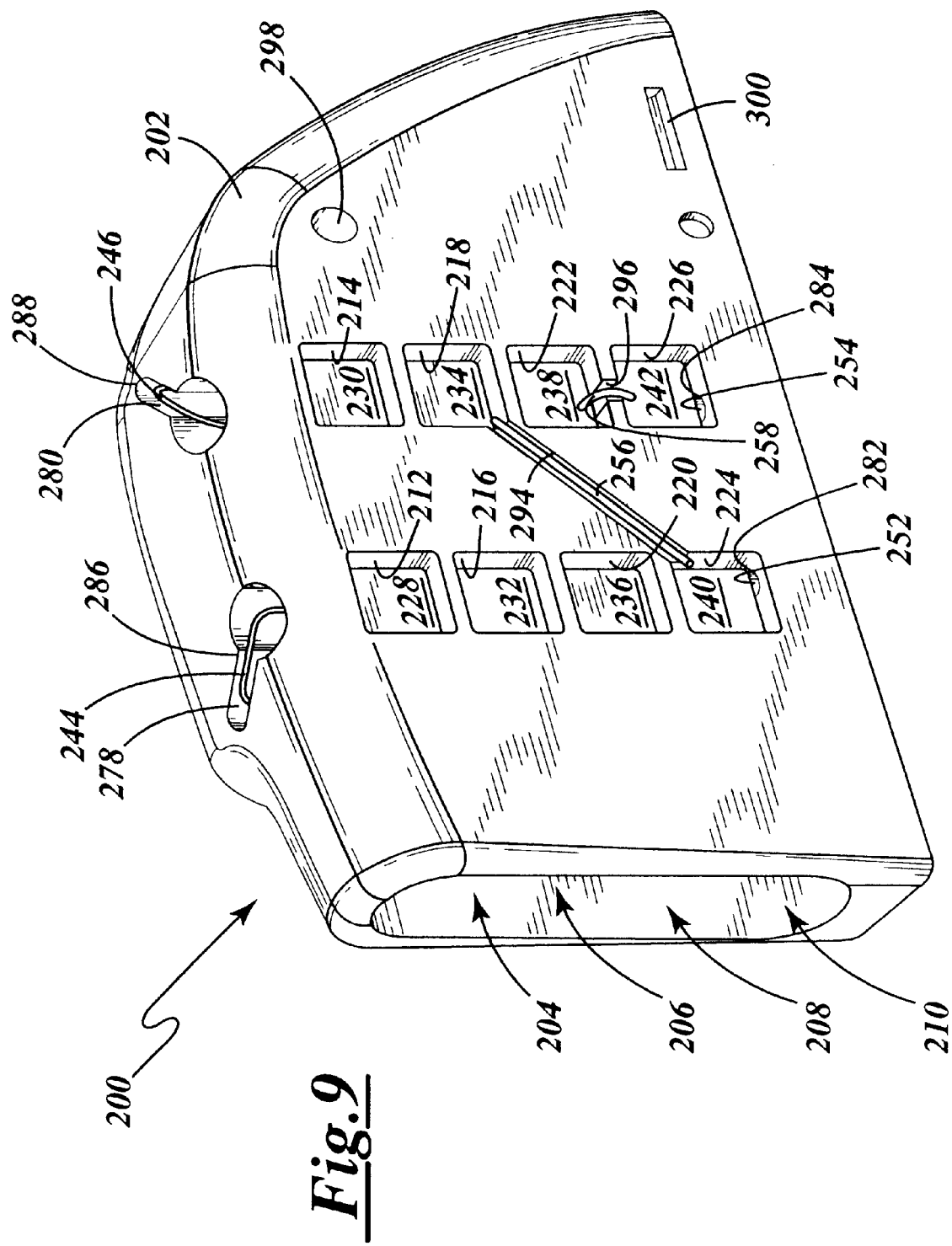
FIG. 9 is a front perspective view of a quadruple port header housing of the present invention.
Figure 10:
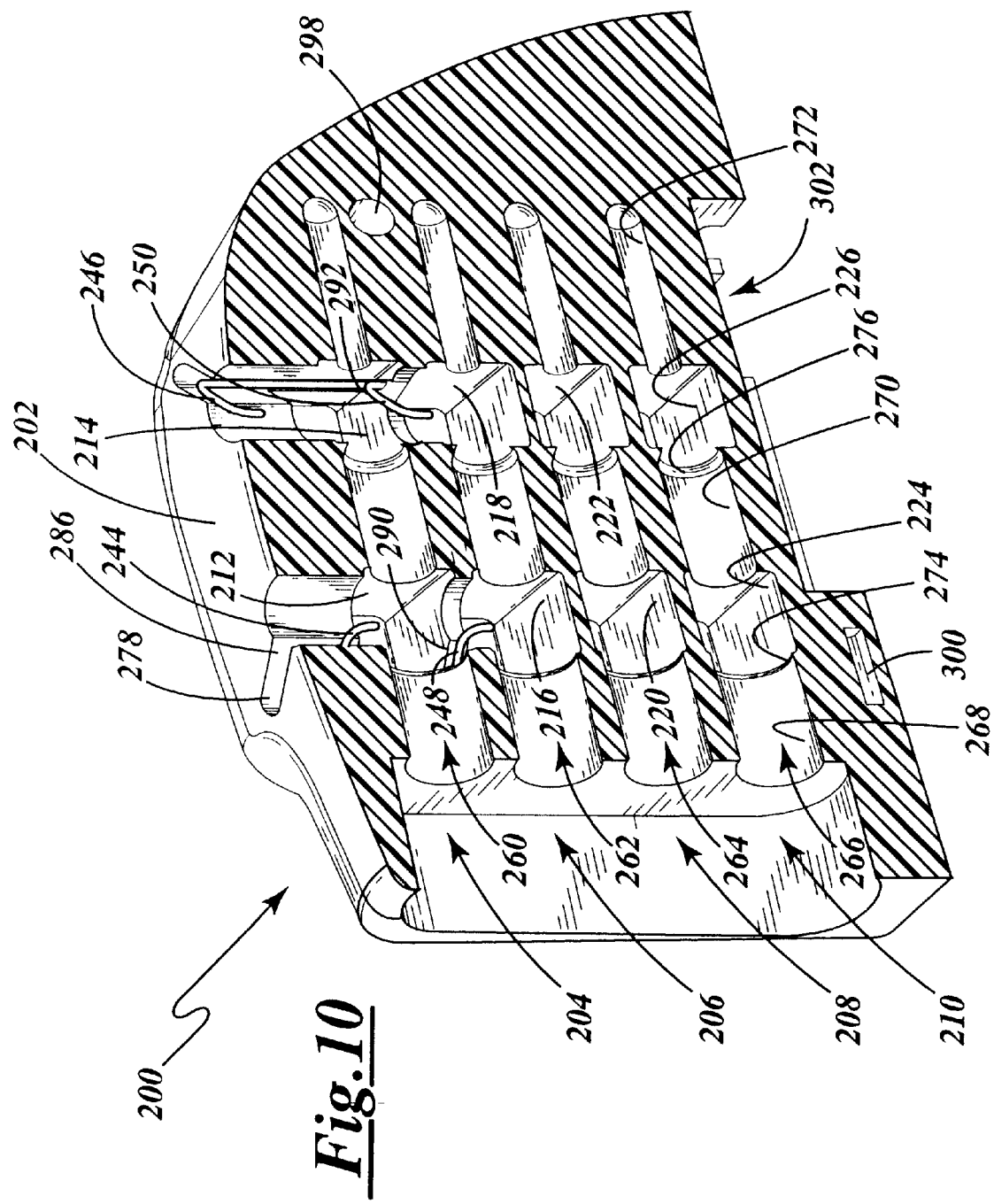
FIG. 10 is a partial sectional view of the quadruple port header housing as shown in FIG. 9, with the terminal blocks removed for clarity.

Referring now to FIGS. 9–11, a quadruple port header assembly is shown. The header assembly 200 generally includes a non-conductive housing 202, ports 204–210, aperatures 212–226 intersecting respective ports 204–210, electrically conductive terminal blocks 228–242 retained in corresponding apertures 212–226, feedthrough wires 244–254, and jumper wires 256–258. A seal plug of known suitable construction may be used to plug any unused ports.

The housing 202 is preferably manufactured from a non-conductive medical grade polymer of known suitable composition, wherein the ports 204–210 and apertures 212–226 are formed into the housing 202. Each port 204–210 has a central bore, 260–266 respectively, adapted for receiving the terminal end of a lead 60. The corresponding bore 260–266 of each port 204–210 extends into the housing 202 from a side surface of the housing 202 toward but short of an opposite side surface. Each bore may be tapered or stepped having varying diameters to thereby fittingly receive the shape and size of the terminal end of the lead 60 (examples of suitable leads are further shown in FIGS. 5 and 6), wherein the largest diameter or step 268 may be approximately equal to the outer diameter of the lead 60 body, the middle diameter or step 270 being equal to the diameter of the lead's conductive ring 70, and the smallest diameter or step 272 may be dimensioned to receive the terminal pin 68 of the lead 60 (see FIGS. 5 and 10).

Apertures 212 and 214 intersect bore 260, apertures 216 and 218 intersect bore 262, apertures 220 and 222 intersect bore 264, and apertures 224 and 226 intersect bore 266 (see FIG. 10). Electrically conductive terminal blocks 228–242 are positioned within corresponding apertures 212–226 (see FIG. 9). Although terminal block 32 is shown in FIG. 7, those skilled in the art will appreciate that terminal blocks 228–242 may be of similar suitable construction. Each terminal block 228–242 has a bore 72 extending therethrough, wherein the bore 72 of each terminal block 228–242 alligns with the corresponding bore 260–266 of the respective port 204–210. Adjacent the intersection between the bore 260–266 and respective apertures 212–226, tapering annular lips 274 and 276 extend perpendiculary inward from each bore 260–266. When a lead 60 is plugged into a port 204–210, shoulder seals 80 and 82 of the lead 60 engage the respective lips 274 and 276 thereby sealingly engaging the lead 60 to the housing 202 and electrically isolating various segments of the lead 60.

Without any limitation intended, the terminal blocks 228–242, terminal pin 68, ring 70, feedthrough wires 244–254 and jumper wires 256–258 are manufactured from titanium or other conductive material sufficient to meet medical standards and all requirements of current transmission. The housing 202, insulative lead 60 body and shoulder seals 80–82 are manufactured from a known polymer or other elastomeric non-conductive material commonly used in the manufacture of implantable pacing/defibrillating devices and leads.

A conduit is formed in the housing for each feedthrough wire. Conduits 278 and 280 extend from the bottom of the housing through to the opposite top side of the housing (see FIGS. 9–10). Grooves 286 and 288 interconnect conduits 278–280 with apertures 212–214 respectively and grooves 290–292 interconnect conduits 278–280 with apertures 216–218. Feedthrough wires 244 and 248 extend from the bottom of the housing up through conduit 278, and feedthrough wires 246 and 250 extend from the bottom of the housing up through conduit 280. Feedthrough 244 extends through groove 286 and is attached to the corresponding terminal block 228, feedthrough 246 extends through groove 288 and is attached to the corresponding terminal block 230, feedthrough 248 extends through groove 290 and is attached to the corresponding terminal block 232, and feedthrough 250 extends through groove 292 and is attached to the corresponding terminal block 234. Conduits 282 and 284 extend from the bottom of the housing 202 and into apertures 224 and 226 respectively (see FIG. 10). Feedthrough wires 252 and 254 extend through conduits 282 and 284, interconnecting the electronic circuit of the pulse generator with the corresponding terminal blocks 240 and 242.

A plurality of channels 294 and 296 are formed in the housing extending between and interconnecting aperture 218 to aperture 224 and aperture 222 to aperture 226 respectively (see FIG. 9). A jumper wire 256 may be positioned within channel 294 to thereby interconnect terminal block 234 to terminal block 240 and jumper wire 258 may be positioned within channel 296 to thereby interconnect terminal block 238 to terminal block 242. Thus, jumper wire 256 may interconnect the conductive ring 70 of a lead positioned in port 210 with the terminal pin 68 of a lead positioned in port 206. Likewise, jumper wire 258 may interconnect the terminal pin 68 of a lead positioned in port 208 with a terminal pin 68 of a lead positioned in port 210. Medical adhesive or epoxy may be applied to each of the exposed terminal block 228–242 surfaces and the channels 294 and 296 to thereby isolate the terminal blocks and jumper wires.

A passage 298 extends through the housing 202 and is adapted for receiving sutures therethrough, thereby providing a means for securing the housing 202 of the cardiac rhythm management device within a surgically formed pocket in the patient. Slots 300 are formed in a bottom portion of the housing 202 and are adapted for engaging with tabs (not shown) which extend from the casing of the cardiac rhythm management device, to thereby sealably secure the housing to the casing. Portions of the housing form voids, as at 302 (see FIG. 10), to thereby reduce both the weight of the housing 202 and the amount of materials required for the housing 202.

Having described the constructional features of the present invention, the mode of use will next be presented. During the pacing of a patient's heart, it may be desirable to transmit simultaneously from a pulse generator an identical electrical signal through two or more leads electrically coupled to the pulse generator. For example, during CHF therapy it is believed that the left and right ventricles may be effectively paced by transmitting simultaneously the same pacing signal to both the left and right ventricle. The header assembly of the present invention may be utilized to electrically couple two or more leads to thereby allow simultaneous transmission of an identical signal through the leads. For example, a pacing signal which is sent to the right ventricle could also be used to simultaneously pace the left ventricle by connecting a jumper wire as described above. Hence, independent pacing signals to the left ventricle and right ventricle would not be required to simultaneously pace the left and right ventricles.

Utilizing the header assembly as shown in FIGS. 1–4, a right atrial bi-polar lead may be inserted into upper port 14, a right ventricle bi-polar lead may be inserted into lower port 18 and a left ventricle uni-polar or bi-polar lead may be inserted into middle port 16. In such a case, a negatively charged right atrium feedthrough wire attaches to the terminal block 34, and a positively charged right atrium feedthrough wire attaches to terminal block 32. The negatively charged right ventricle feedthrough wire attaches to the terminal block 42, and the positively charged right ventricle feedthrough wire attaches to terminal block 40. Jumper wire 52 may electrically couple, for example terminal blocks 38 and 42. The pacing signal transmitted through the terminal pin of the left ventricle lead will be the same as that transmitted to the terminal pin of the right ventricle lead.

This invention has been described herein in considerable detail in order to comply with the patent statutes and to provide those skilled in the art with the information needed to apply the novel principles and to construct and use such specialized components as are required. However, it is to be understood that the invention can be carried out by specifically different devices, and that various modifications, both as to the equipment details and operating procedures, can be accomplished without departing from the scope of the invention itself.

What is claimed is:

1. A header assembly of an implantable device capable of electrically and mechanically coupling at least two electrical sensing and/or pacing leads and adapted for both sealably engaging a casing of the implantable device and electrically coupling an electronic circuit and power supply contained within the casing, which generates an electrical pulse for stimulating tissue of a patient, said header assembly comprising:

(a) a housing coupled to the casing of the implantable device, said housing having at least two ports extending from a side surface of said housing toward but short of an opposite side surface, wherein each port is adapted for sealably receiving a terminal end of a lead, each said port having first and second spaced apart apertures intersecting the port;

(b) an electrically conductive terminal block positioned within each aperture, each said terminal block having a means for securing the terminal end of the lead to a respective terminal block; and (c) a jumper wire positioned within a channel formed in the housing which interconnects preselected apertures, at least a portion of said channel being accessible from an external surface of said housing, said jumper wire being electrically coupled to corresponding terminal blocks contained within the preselected apertures.

2. The header assembly as recited in claim 1, wherein each said bore and channel is filled with a sealing medical adhesive.

3. The header assembly as recited in claim 1, comprising a first, second and third port, each said port extending through said housing from a side surface of said housing toward, but short of, an opposite side surface.

4. The header assembly as recited in claim 3, wherein the first port is adapted for receiving a bi-polar right atrial lead.

5. The header assembly as recited in claim 4, wherein the second port is adapted for receiving a bi-polar left ventricular lead.

6. The header assembly as recited in claim 5, further including a jumper wire positioned within a channel interconnecting apertures of the first and second ports and electrically coupling corresponding terminal blocks contained therein.

7. The header assembly as recited in claim 3, wherein the first port is adapted for receiving a uni-polar right atrial lead.

8. The header assembly as recited in claim 3, wherein the second port is adapted for receiving a uni-polar left ventricular lead.

9. The header assembly as recited in claim 3, wherein the second port is adapted for receiving a bi-polar left ventricular lead.

10. The header assembly as recited in claim 3, wherein the third port is adapted for receiving a bi-polar right ventricular lead.

11. The header assembly as recited in claim 3, wherein the third port is adapted for receiving a uni-polar right ventricular lead.

12. The header assembly as recited in claim 1, comprising a first, second, third and fourth port, each said port extending from a side surface of said housing toward, but short of, an opposite side surface.

13. The header assembly as recited in claim 12, wherein the first port is adapted for receiving a bi-polar right atrial lead.

14. The header assembly as recited in claim 12, wherein the first port is adapted for receiving a uni-polar right atrial lead.

15. The header assembly as recited in claim 12, wherein the second port is adapted for receiving a uni-polar left ventricular lead.

16. The header assembly as recited in claim 15, wherein the third port is also adapted for receiving a uni-polar left ventricular lead.

17. The header assembly as recited in claim 16, further including a jumper wire positioned within a channel interrconnecting apertures of the second and fourth ports and electrically coupling corresponding terminal blocks contained therein.

18. The header assembly as recited in claim 16, further including a jumper wire positioned within a channel interrconnecting apertures of the third and fourth ports and electrically coupling corresponding terminal blocks contained therein.

19. The header assembly as recited in claim 12, wherein the fourth port is adapted for receiving a bi-polar right ventricular lead.

20. The header assembly as recited in claim 12, wherein the fourth port is adapted for receiving a uni-polar right ventricular lead.

21. A header assembly of an implantable device capable of electrically and mechanically coupling at least two electrical sensing and/or pacing leads and adapted for both sealably engaging a casing of the implantable device and electrically coupling an electronic circuit and power supply contained within the casing, which generates an electrical pulse for stimulating tissue of a patient, said header assembly comprising:

(a) a housing coupled to the casing of the implantable device, said housing having at least two ports extending from a side surface of said housing toward but short of an opposite side surface, wherein each port is adapted for sealably receiving a terminal end of a lead, each said port having first and second spaced apart apertures intersecting the port;

(b) an electrically conductive terminal block positioned within each aperture, each said terminal block having a means for securing the terminal end of the lead to a respective terminal block; and (c) a jumper wire positioned within a channel formed in the housing which interconnects preselected apertures, said channel extending inward from an external surface of said housing, said jumper wire being electrically coupled to corresponding terminal blocks contained within the preselected apertures.

22. The header assembly as recited in claim 21, comprising a first, second and third port, each said port extending through said housing from a side surface of said housing toward, but short of, an opposite side surface.

23. The header assembly as recited in claim 22, wherein the first port is adapted for receiving a bi-polar right atrial lead.

24. The header assembly as recited in claim 23, wherein the second port is adapted for receiving a bi-polar left ventricular lead.

25. The header assembly as recited in claim 24, further including a jumper wire positioned within a channel interconnecting apertures of the first and second ports and electrically coupling corresponding terminal blocks contained therein.

26. The header assembly as recited in claim 22, wherein the first port is adapted for receiving a uni-polar right atrial lead.

27. The header assembly as recited in claim 22, wherein the second port is adapted for receiving a uni-polar left ventricular lead.

28. The header assembly as recited in claim 22, wherein the second port is adapted for receiving a bi-polar left ventricular lead.

29. The header assembly as recited in claim 22, wherein the third port is adapted for receiving a bi-polar right ventricular lead.

30. The header assembly as recited in claim 22, wherein the third port is adapted for receiving a uni-polar right ventricular lead.

* * * * *